(12) United States Patent
Scott et al.

(10) Patent No.: US 7,572,296 B2
(45) Date of Patent: Aug. 11, 2009

(54) PROSTHESIS

(75) Inventors: Robert A. Scott, Christian Malford (GB); Robert John Andrew Bigsby, Penarth (GB)

(73) Assignee: Biomet UK Limited, South Glamorgan (GB)

( * ) Notice: Subject to any disclaimer, the term of this patent is extended or adjusted under 35 U.S.C. 154(b) by 56 days.

(21) Appl. No.: 11/600,323

(22) Filed: Nov. 15, 2006

(65) Prior Publication Data
US 2008/0114459 A1    May 15, 2008

(51) Int. Cl.
*A61F 2/32* (2006.01)
(52) U.S. Cl. .................. 623/22.28; 623/22.21
(58) Field of Classification Search .............. 623/22.21, 623/22.24, 22.11, 22.15, 22.17, 22.18, 22.25
See application file for complete search history.

(56) References Cited

U.S. PATENT DOCUMENTS

| | | | |
|---|---|---|---|
| 4,173,797 A | 11/1979 | Langlais et al. | |
| 4,743,262 A | 5/1988 | Tronzo | |
| 4,955,919 A * | 9/1990 | Pappas et al. | 623/22.26 |
| 5,041,140 A | 8/1991 | Teinturier | |
| 5,507,824 A * | 4/1996 | Lennox | 623/22.25 |
| 5,549,691 A | 8/1996 | Harwin | |
| 5,645,606 A | 7/1997 | Oehy et al. | |
| 5,931,870 A * | 8/1999 | Cuckler et al. | 623/22.21 |
| 2005/0246026 A1 * | 11/2005 | Lewis et al. | 623/20.15 |

FOREIGN PATENT DOCUMENTS

| | | |
|---|---|---|
| DE | 3129174 A | 2/1983 |
| DE | 88 07 947 U | 8/1988 |
| DE | 296 14 342 U | 10/1996 |
| DE | 101 59 677 A1 | 6/2003 |
| EP | 1053723 | 11/2000 |
| EP | 1532946 | 5/2005 |
| EP | 1702589 | 9/2006 |
| FR | 2793137 | 11/2000 |
| FR | 2819172 | 7/2002 |
| GB | 1409051 | 10/1975 |
| GB | 2424187 | 9/2006 |

* cited by examiner

*Primary Examiner*—Thomas J Sweet
*Assistant Examiner*—Yashita Sharma
(74) *Attorney, Agent, or Firm*—Harness, Dickey (57) ABSTRACT

A prosthesis to be implanted within a bone comprises a shell and a liner that fits within the shell. The shell comprises a bone engaging region which terminates at a first plane, and a non-bone engaging region which extends out of the first plane and at least partially defines an open mouth of the shell.

17 Claims, 7 Drawing Sheets

PRIOR ART

PROSTHESIS

FIELD

This invention relates to a prosthesis and particularly but not exclusively relates to an acetabular prosthesis for a hip joint.

BACKGROUND

Adetabular prostheses, comprising at least an outer shell and an inner bearing, are commonly used in total hip replacement surgery. Ceramic bearings are often preferred to the Ultra High Molecular Weight Polyethylene alternatives for their superior wear characteristics in normal use. However, ceramic bearings, due to their brittle nature, are particularly sensitive to excessive loading on the rim of the bearing. In its mildest form, rim loading appears as a distinctive stripe of wear on the femoral head and acetabular bearing, known as "stripe wear". At its most severe, rim loading can lead to failure of the acetabular bearing. Rim loading is caused as the femoral head briefly separates from the acetabular shell and then contacts the rim of the bearing as it reseats into the shell. This process is known as microseparation, and the degree of separation is closely related to the orientation of the acetabular shell. The more closely the open face of the shell is aligned to a vertical axis, the greater the microseparation, and hence the greater the rim damage.

The success of ceramic bearings is thus heavily dependent on operative technique and the anatomy of the patient concerned. While the recommendation is to implant the prosthesis at a reasonably closed or reduced angle in order to limit microseparation, this is not possible for all patients. If a patient's natural acetabulum is close to vertical, the surgeon is forced to open the face of the shell in order to obtain sufficient bone contact.

Microseparation in the case of UHMWPE bearings can be compensated for by extending the bearing past the rim of the supporting shell in order to provide a larger bearing surface within which the femoral head can articulate. This option is not, however, available for ceramic bearings, due to the danger of loading an unsupported area of ceramic.

SUMMARY

According to the present invention, there is provided a prosthesis to be implanted within a bone, the prosthesis comprising a shell and a liner that fits within the shell, the shell comprising a bone engaging region that terminates at a first plane, and a non-bone engaging region that extends out of the first plane and at least partially defines an open mouth of the shell.

Preferably, when the prosthesis is implanted, the first plane is substantially coincident with a surface of the surrounding bone.

The shell can thus be implanted with good bone contact within a substantially vertical acetabulum and still present a relatively closed bearing surface that is less susceptible to microseparation than the prior art prostheses.

The angle between the first plane of the shell and a second plane defined by a mouth of the non-bone engaging region may be between 5 and 40 degrees.

Preferably, an inner surface of the liner is substantially hemispherical in shape.

The mouth of the non-bone engaging region may entirely define the mouth of the shell. Alternatively, the mouth of the non-bone engaging region may define only a portion of the mouth of the shell.

An equatorial plane of the liner may be angled with respect to the first and second planes of the shell. Alternatively, the equatorial plane of the liner may be parallel with the first or with the second plane of the shell.

An inner surface of the liner may have a substantially hemispherical first region that terminates at an equatorial plane and may have a second region that extends out of the equatorial plane and may at least partially define an open mouth of the liner.

The liner may be seated within the shell such that the mouth of the liner is coterminous with the mouth of the shell.

The shell may engage with the bone via a supporting cup. The mouth of the cup may be substantially coincident with a surrounding surface of the bone. The bone engaging region of the shell may be partially cut away, such that the shell comprises a tube or sleeve.

Preferably, the bone is an acetabulum. The liner may be made from a ceramic material. The shell may be made from a metal. The supporting cup may also be made from a metal.

Advantageously, the use of a liner having first and second regions within a shell of the present invention permits a larger liner to be used within a given size of shell. The wall thickness of the liner can be reduced, thus presenting a larger bearing surface to a femoral head within a given size of shell. The size of acetabular shell required for a given femoral head may therefore be reduced, reducing the amount of acetabular bone tissue that has to be removed prior to implantation.

According to another aspect of the present invention, there is provided a method of implanting a prosthesis of the present invention into an acetabulum, comprising fixing the prosthesis such that the said first plane is substantially coincident with an outer surface of the acetabulum. In this manner, a surgeon can achieve good bone contact across the external surface of the shell, whilst maintaining a reduced angle at the open face of the bearing.

According to another aspect of the present invention, there is provided a prosthesis comprising a shell and a liner that fits within the shell, wherein the shell comprises a substantially hemispherical bone engaging region and a support region which extends from the bone engaging region such that an open face of the shell is angled with respect to an equatorial plane of the bone engaging region.

The liner may be seated within the shell such that an outer surface of the liner and an inner surface of the support region are in contact. The hemispherical liner may be rotated from its usual position within a hemispherical shell around the centre of rotation of the bearing surface.

Alternatively, the liner may have a substantially hemispherical first region and a second region which extends from the first region such that the open face of the liner is angled with respect to the equatorial plane of the first region. The liner may be seated within the shell such that the open face of the liner and the open face of the shell are aligned.

DRAWINGS

For a better understanding of the present invention, and to show more clearly how it may be carried into effect, reference will now be made, by way of example, to the accompanying drawings, in which.

DETAILED DESCRIPTION

Figure 1:
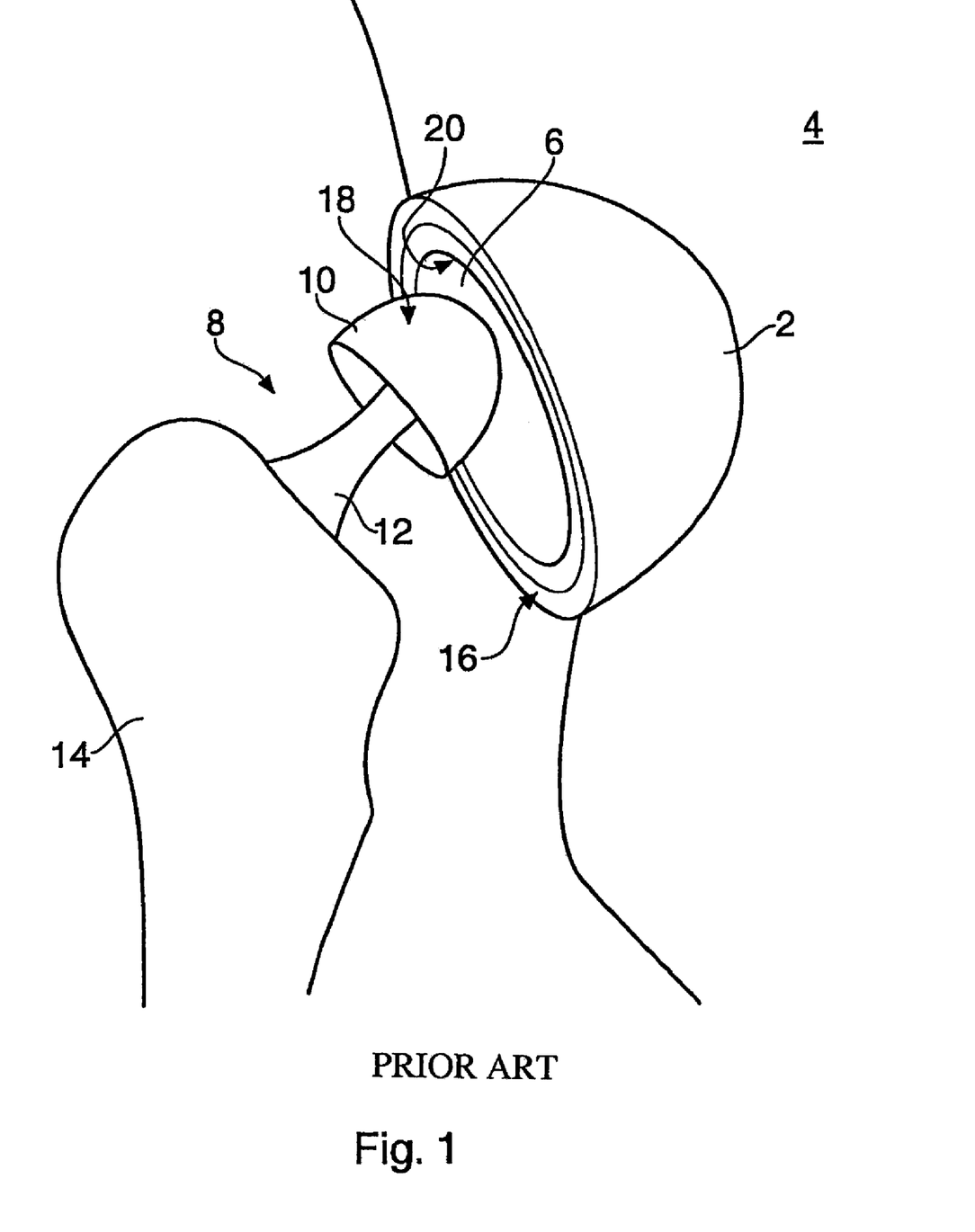
FIG. 1 is a perspective view of a prior art prosthesis in use.

Referring to FIG. 1, a conventional acetabular shell 2 is implanted within an acetabulum 4. The shell 2 contains a bearing liner 6, which is has a substantially hemispherical bearing surface. A femoral prosthesis 8, comprising a femoral head 10 and a neck 12 is implanted into the proximal end of a femur 14. The acetabulum illustrated provides an opening that is almost vertically oriented. In order for the shell 2 to be properly seated within the acetabulum, the mouth 16 of the shell is opened, such that the mouth 16 is orientated in a plane that is at an angle of greater than 45 degrees to the horizontal. Stripe wear develops in the regions 18 and 20 on the femoral head 10 and acetabular liner 6 respectively.

Figure 2:
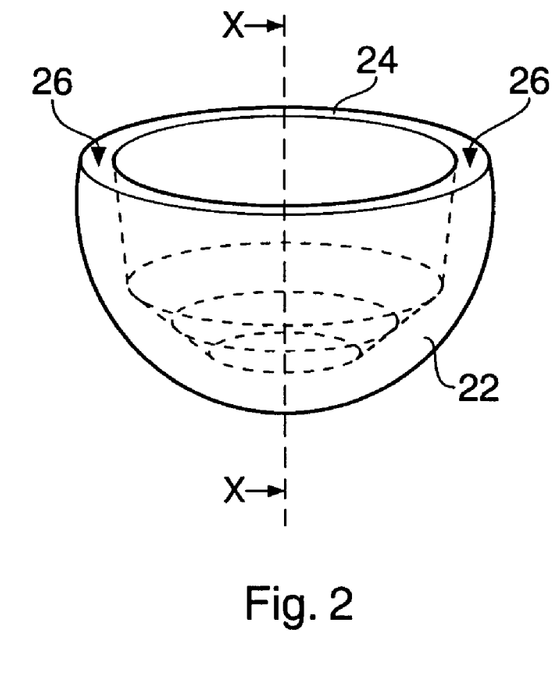
FIG. 2 is a side view of an acetabular shell.
Figure 3:
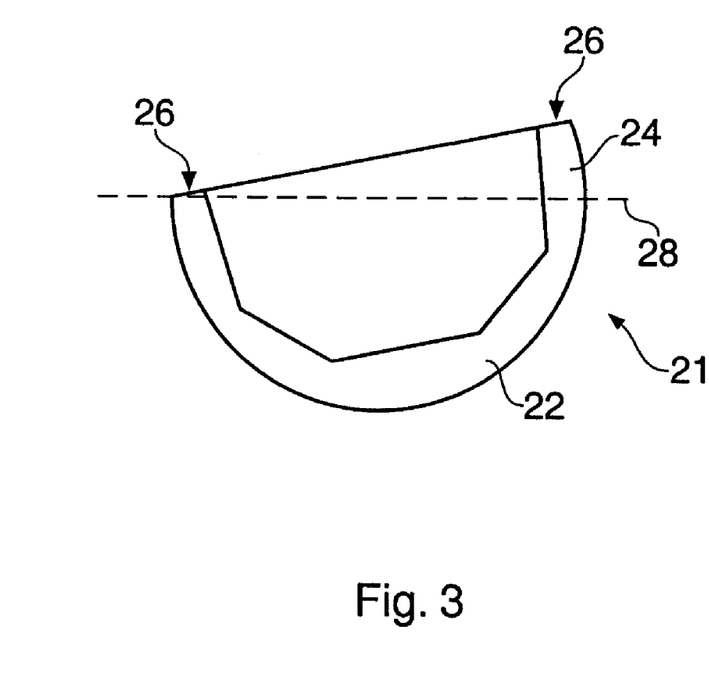
FIG. 3 is a sectional view along the line XX in FIG. 2.

Referring to FIGS. 2 and 3, an acetabular shell 21 comprises a bone engaging region 22 and a non-bone engaging region 24. The bone engaging region 22 terminates at a first plane 28. The non-bone engaging region 24 extends from the plane 28 of the bone engaging region 22 to define a mouth 26 of the shell 21.

Figure 4:
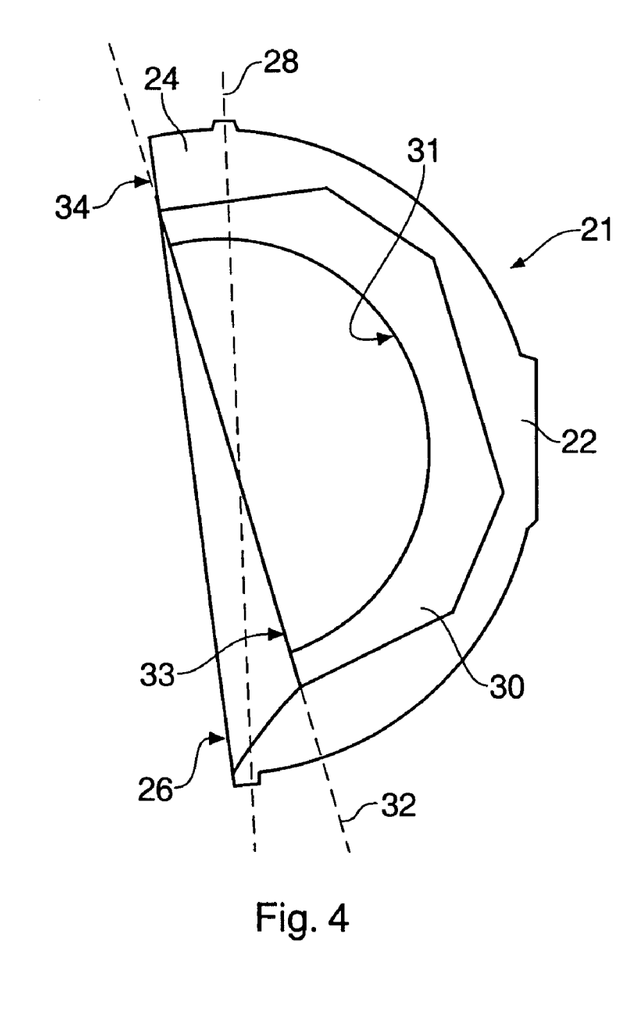
FIG. 4 is a sectional view of an acetabular shell and a bearing liner.
Figure 5:
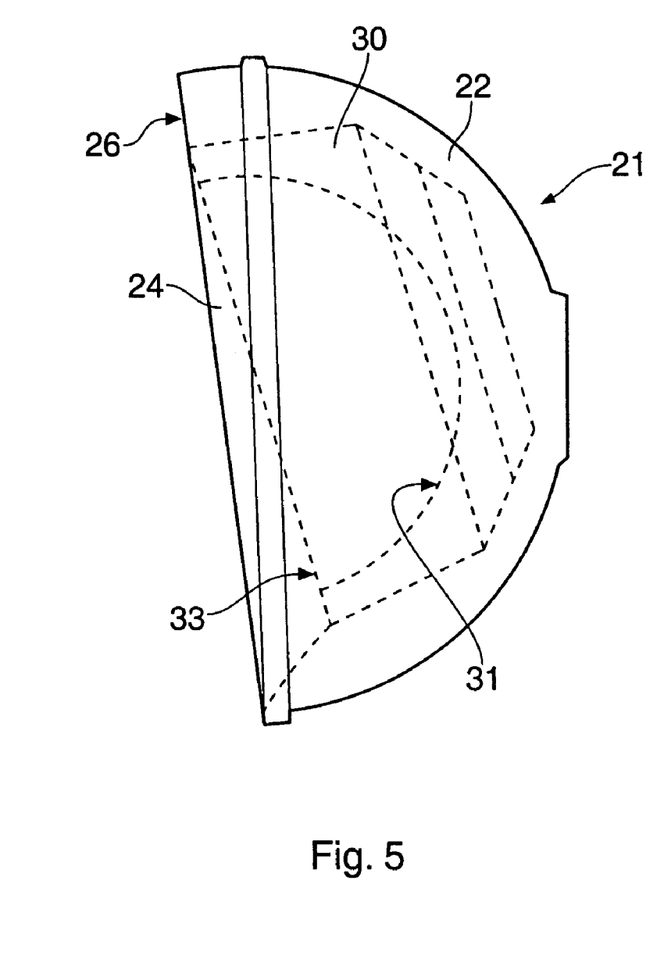
FIG. 5 is a side view of the prosthesis of FIG. 4.

Referring to FIGS. 4 and 5, in one embodiment, a liner 30 is disposed within the shell 21. The liner 30 has a substantially hemispherical inner bearing surface 31 and a mouth 33. The mouth 33 is defined by an equatorial plane 32 of the liner 30. The liner 30 is disposed within the shell 21 such that the mouth 33 of the liner 30 is not aligned with the first plane 28 of the shell 21 and is also not aligned with the open mouth 26 of the shell 21. The liner is positioned to achieve maximum contact between the internal surface of the non-bone engaging region 24 and the external surface of the liner 30 at the proximal end 34 of the shell 21.

Figure 6:
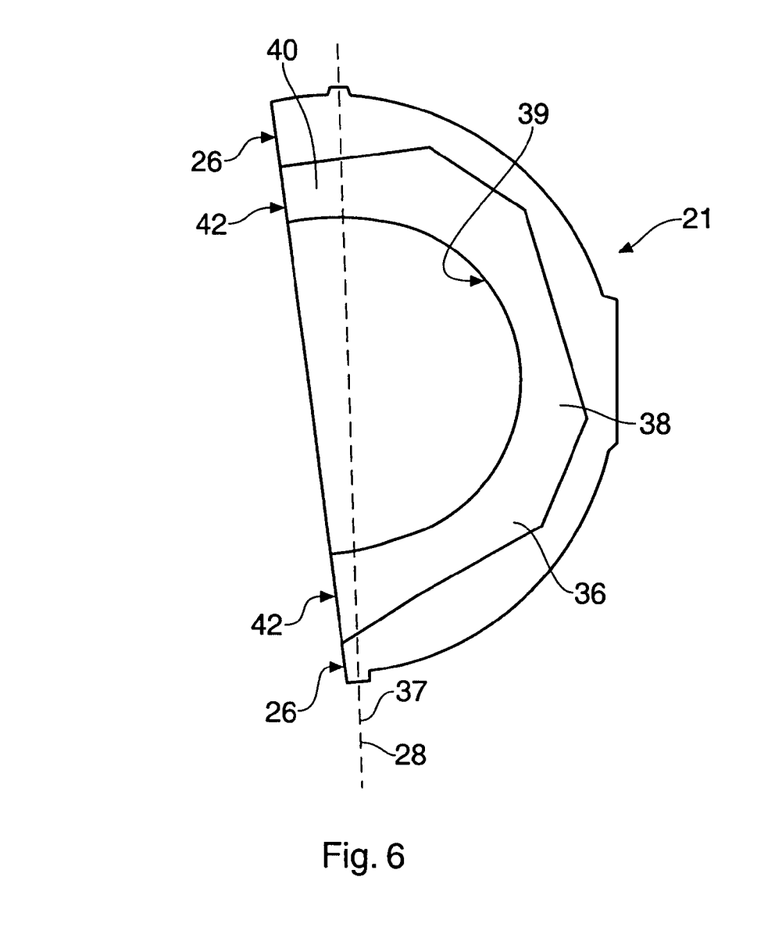
FIG. 6 is a sectional view of an acetabular shell and an alternative bearing liner.

Referring to FIG. 6, in another embodiment, a liner 36 is disposed within the shell 21. The liner 36 comprises a first region 38, which terminates in a plane 37 and has a substantially hemispherical inner bearing surface 39, and a second region 40, that projects from the plane 37 to define a mouth 42 of the liner 36. The liner 36 is positioned such that the mouth 42 of the liner is coterminous with the mouth 26 of the shell.

Figure 7:
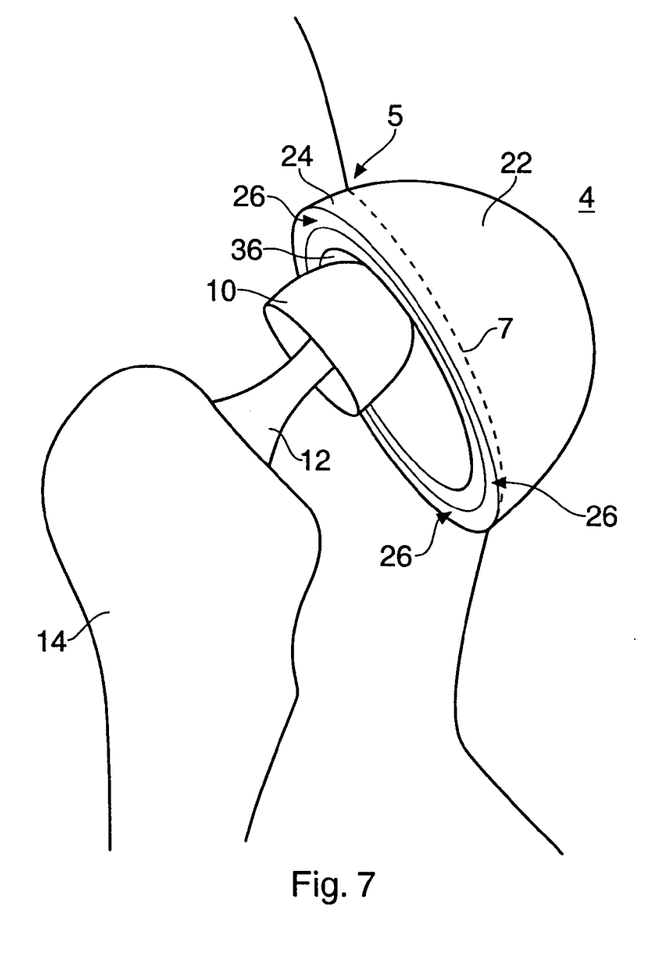
FIG. 7 is a perspective view of the prosthesis of FIG. 6 in use.

Referring to FIG. 7, in use, the shell 21 is implanted in an acetabulum such that the bone engaging region 22 is in contact with acetabulum 4 and the non-bone engaging region 24 protrudes past the rim 5 of the acetabulum at the proximal end. The mouth 26 of the shell 21 is thus at a greater angle to the vertical than the open face 7 of the acetabulum 4. The head 10 of the femoral prosthesis is received more fully within the interior of the liner 36 when compared with the prior art prosthesis of FIG. 1. The increased angle of the face 26 reduces the incidence of microseparation and therefore reduces wear in the regions 18 and 20 (both hidden in FIG. 7) of the femoral head 10 and liner 36 respectively.

Figure 8:
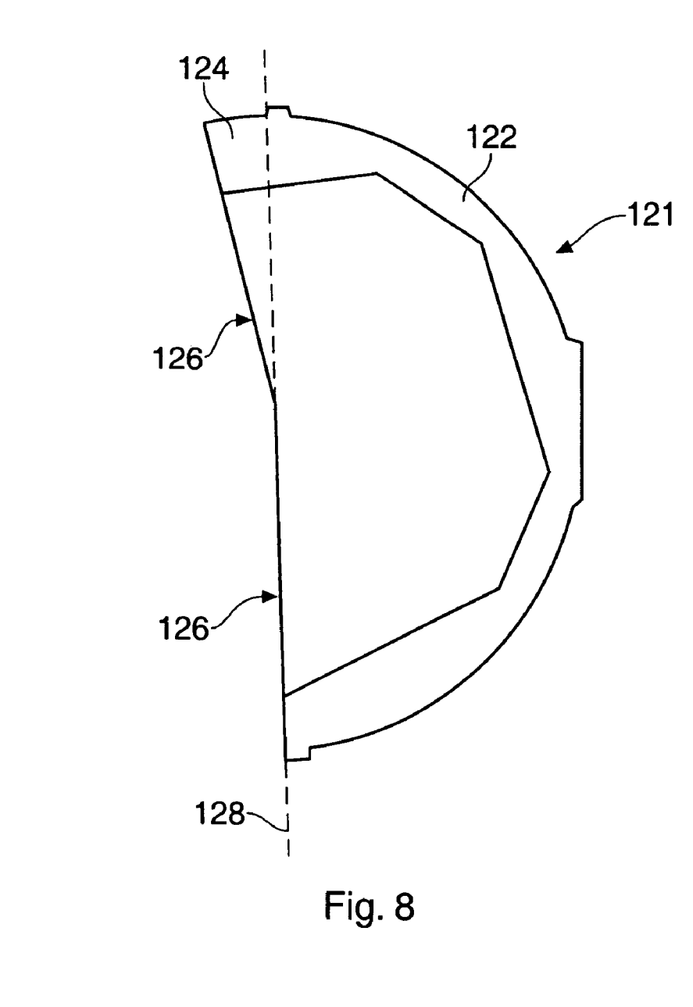
FIG. 8 is a sectional view an alternative acetabular shell.

Referring to FIG. 8, an acetabular shell 121 comprises a bone engaging region 122 and a non-bone engaging region 124. The bone engaging region 122 terminates at a first plane 128. The non-bone engaging region 124 extends from the plane 128 of the bone engaging region 122. The non-bone engaging region 124 is superimposed over only a portion of the bone engaging region 122, such that a mouth 126 of the shell 121 is defined both by the bone engaging region 122 and the non-bone engaging region 124.

Figure 9:
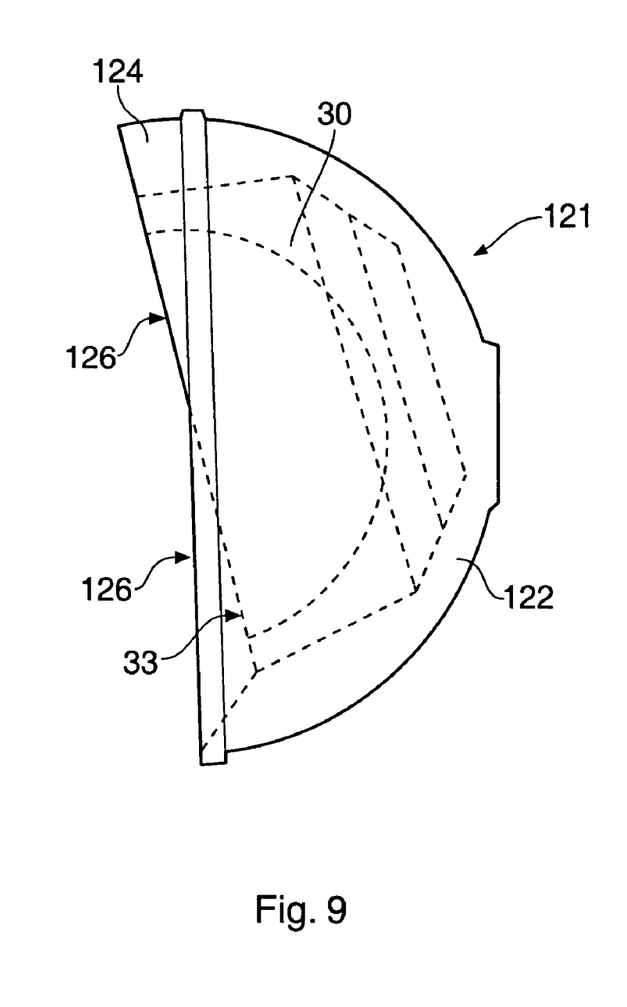
FIG. 9 is a side view of the shell of FIG. 8 and the bearing liner of FIGS. 4 and 5.

Referring to FIG. 9, in one embodiment, the liner 30 may be received within the shell 121. The liner 30 is disposed within the shell 121 such that the mouth 33 of the liner 30 is substantially aligned with that portion of the mouth 126 of the shell 121 that is formed by the non-bone engaging region 124. Maximum contact between the internal surface of the non-bone engaging region 124 and the external surface of the liner 30 at the proximal end 34 of the shell 21 is thus achieved.

Figure 10:
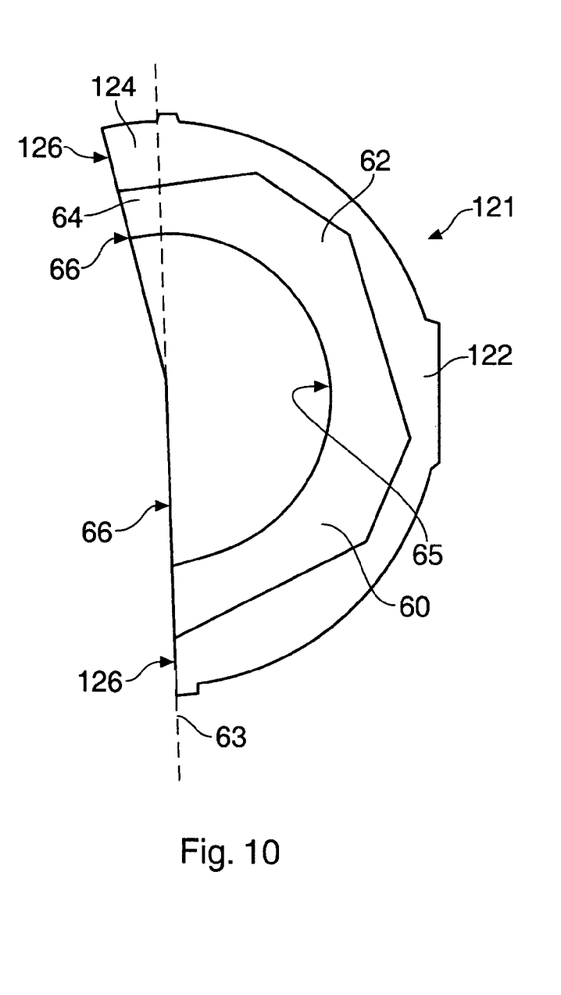
FIG. 10 is a sectional view of the shell of FIG. 8 and another alternative bearing liner.

Referring to FIG. 10, in another embodiment, a liner 60 may be received within the shell 121. The liner 60 comprises a first region 62, which terminates in a plane 63 and has a substantially hemispherical inner bearing surface 65, and a second region 64, that projects from the plane 63. The second region 64 extends over only a portion of the first region 62, such that a mouth 66 of the liner 60 is defined both by the first region 62 and the second region 64. The liner 60 is positioned such that the mouth 66 of the liner is coterminous with the mouth 126 of the shell.

Figure 11:
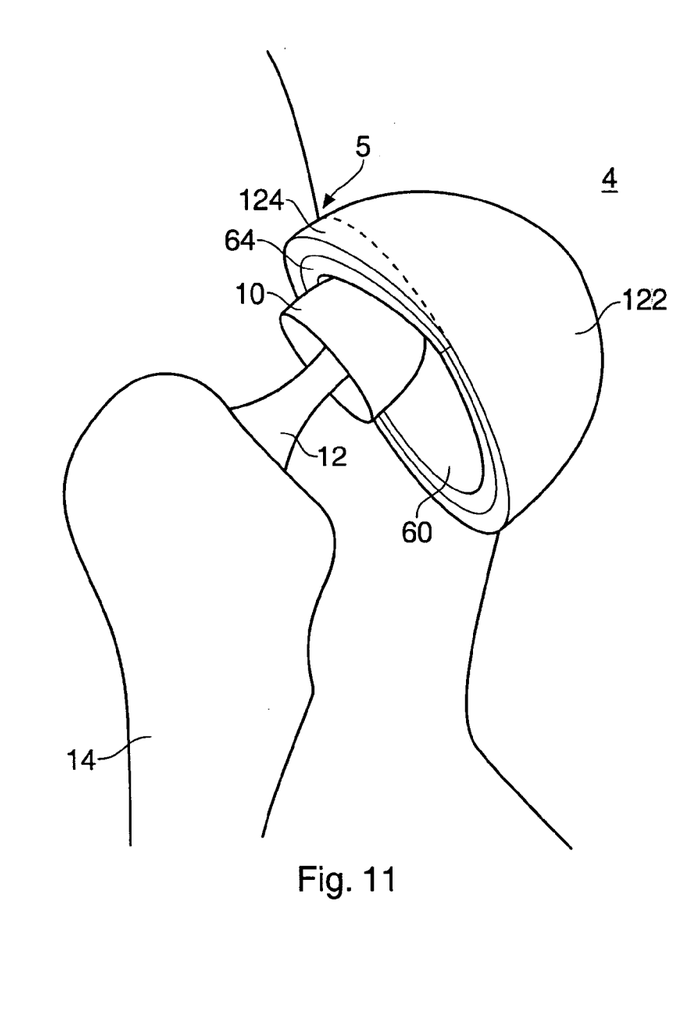
FIG. 11 is a perspective view of the prosthesis of FIG. 10 in use.

Referring to FIG. 11, in use, the shell 121 is implanted in an acetabulum such that the bone engaging region 122 is in contact with acetabulum 4 and the non-bone engaging region 124 protrudes past the rim 5 of the acetabulum at the proximal end. The proximal portion of the mouth 126 of the shell 121 is at a greater angle to the vertical than in a prior art prosthesis, as illustrated in FIG. 1. The non-bone engaging region 124 of the shell 121 and the second region 64 of the liner 60 provide additional support for the femoral head 10, reducing the incidence of microseparation and associated wear.

Figure 12:
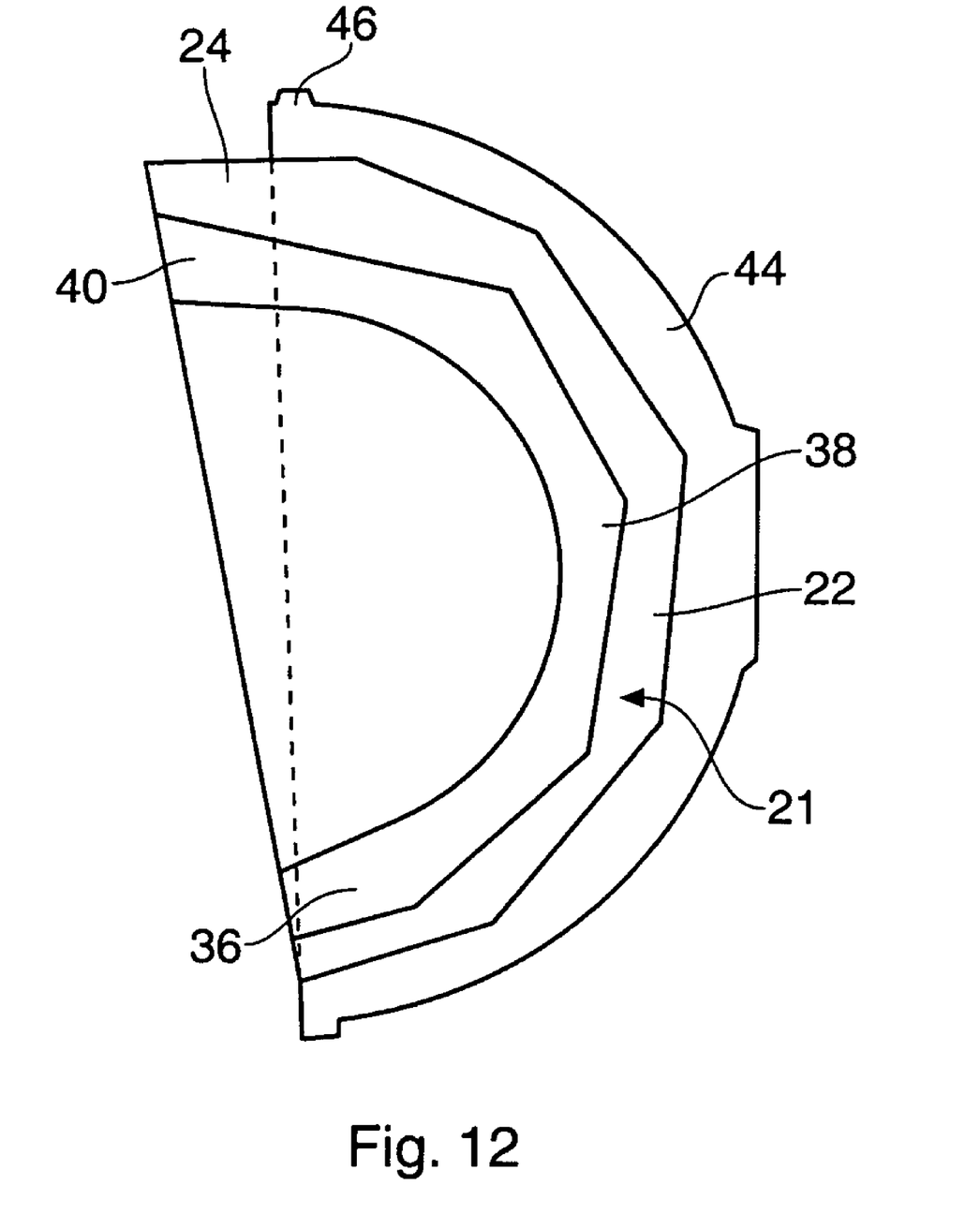
FIG. 12 is a sectional view of an alternative prosthesis.

In an alternative embodiment, illustrated in FIG. 12, the shell 21 is received within a hemispherical cup 44. In use, the cup 44 is implanted within the acetabulum 4 such that the non-bone engaging region 24 of the shell 21 protrudes past the rim 46 of the cup 44 and the rim 5 of the acetabulum 4. The liner 30 or the liner 36 may be received within the shell 21.

Alternatively, the shell 121 and liner 30 or liner 60 may be received within the cup 44.

In an alternative embodiment, not shown, the bone engaging region of the shell may be partially cut away. For example, the portion of the shell furthest from the mouth may be removed, so as to form a second mouth, opposite the first. The shell thus forms a curved tube or sleeve that supports only the tapered region of the liner and that part of the liner that extends beyond the cup.

What is claimed is:

1. A prosthesis to be implanted within a bone, the prosthesis comprising:
  a shell and a liner that fits within the shell, the shell comprising a bone engaging region that terminates at a first plane, and a non-bone engaging region that extends out of the first plane and at least partially defines an open mouth of the shell, said shell further defining an alignment flange disposed at the intersection of the non-bone engaging region and the bone engaging region, wherein the angle between the first plane and a second plane defined by a mouth of the non-bone engaging region is between 5 and 40 degrees, and the mouth of the non-bone engaging region entirely defines the mouth of the shell, and an equatorial plane of the liner is parallel with the second plane of the shell.

2. The prosthesis as claimed in claim 1, wherein an inner surface of the liner is substantially hemispherical in shape.

3. The prosthesis as claimed in claim 1, wherein the liner is seated within the shell such that the mouth of the liner is coterminous with the mouth of the shell.

4. The prosthesis as claimed in claim 1, wherein the mouth of the shell is substantially coincident with a surrounding resected surface.

5. The prosthesis as claimed in claim 1, wherein the bone is an acetabulum.

6. The prosthesis as claimed in claim 1, wherein the liner is made from a ceramic material.

7. The prosthesis as claimed in claim 1, wherein the shell is made from a metal.

8. The prosthesis as claimed in claim 1, wherein the shell is made from a metal.

9. A prosthesis to be implanted within a bone, the prosthesis comprising:
a shell and a liner that fits within the shell, the shell comprising a bone engaging region that terminates at a first plane, and a non-bone engaging region that extends out of the first plane and at least partially defines an open mouth of the shell, said shell further defining an alignment flange disposed at the intersection of the non-bone engaging region and the bone engaging region, wherein an inner surface of the liner has a substantially hemispherical first region that terminates at an equatorial plane and a second region that extends out of the equatorial plane and at least partially defines an open mouth of the liner.

10. The prosthesis as claimed in claim 9, wherein the angle between the first plane and a second plane defined by a mouth of the non-bone engaging region is between 5 and 40 degrees.

11. The prosthesis as claimed in claim 10, wherein the mouth of the non-bone engaging region entirely defines the mouth of the shell.

12. The prosthesis as claimed in claim 11, wherein an equatorial plane of the liner is angled with respect to the first and second planes of the shell.

13. The prosthesis as claimed in claim 11, wherein an equatorial plane of the liner is parallel with the second plane of the shell.

14. The prosthesis as claimed in claim 10, wherein the mouth of the non-bone engaging region defines only a portion of the mouth of the shell.

15. The prosthesis as claimed in claim 14, wherein an equatorial plane of the liner is parallel with the first plane of the shell.

16. A method of implanting a prosthetic into a bone comprising:
providing a shell having a bone engaging region that terminates at a first plane, a non-bone engaging region that extends out of the first plane, and an alignment surface disposed between the bone engaging region and the non-bone engaging region, said non-bone engaging region defining at least a portion of an open mouth defined by the shell;
implanting the prosthetic to position the first plane coincident with a surface of the bone; and
coupling a liner wherein an inner surface of the liner has a substantially hemispherical first region that terminates at an equatorial plane and a second region that extends out of the equatorial plane and at least partially defines an open mouth of the liner to the shell.

17. The method of implanting a prosthesis according to claim 16, wherein implanting the prosthetic is implanting the prosthetic into an acetabulum, and fixing the prosthesis such that the said first plane is substantially coincident with an outer surface of the acetabulum.

* * * * *

UNITED STATES PATENT AND TRADEMARK OFFICE
CERTIFICATE OF CORRECTION

PATENT NO. : 7,572,296 B2
APPLICATION NO. : 11/600323
DATED : August 11, 2009
INVENTOR(S) : Robert A. Scott et al.

It is certified that error appears in the above-identified patent and that said Letters Patent is hereby corrected as shown below:

Delete Title Page, and replace with new Title Page. (Attached)
Col. 1, Line 10, "Adetabular" should be --Acetabular--.
Col. 3, Line 5, after "view", insert --of--.
Col. 3, Line 18, after "which", delete "is".
Col. 5, Lines 13-14, Claim 8, Claim 17 was not deleted and appears as Claim 8 in patent which is a duplicate of Claim 7.
Delete Claim 8, and renumber claims 9-17 as 8-16 consecutively.

Signed and Sealed this

Twenty-fourth Day of November, 2009

David J. Kappos
*Director of the United States Patent and Trademark Office*

(12) United States Patent
Scott et al.

(10) Patent No.: US 7,572,296 B2
(45) Date of Patent: Aug. 11, 2009

(54) PROSTHESIS (75) Inventors: Robert A. Scott, Christian Malford (GB); Robert John Andrew Bigsby, Penarth (GB)

(73) Assignee: Biomet UK Limited, South Glamorgan (GB)

( * ) Notice: Subject to any disclaimer, the term of this patent is extended or adjusted under 35 U.S.C. 154(b) by 56 days.

(21) Appl. No.: 11/600,323

(22) Filed: Nov. 15, 2006

(65) Prior Publication Data

US 2008/0114459 A1    May 15, 2008

(51) Int. Cl.
*A61F 2/32* (2006.01)
(52) U.S. Cl. ............................ 623/22.28; 623/22.21
(58) Field of Classification Search ............ 623/22.21, 623/22.24, 22.11, 22.15, 22.17, 22.18, 22.25
See application file for complete search history.

(56) References Cited

U.S. PATENT DOCUMENTS

| | | | |
|---|---|---|---|
| 4,173,797 A | 11/1979 | Langlais et al. | |
| 4,743,262 A | 5/1988 | Tronzo | |
| 4,955,919 A * | 9/1990 | Pappas et al. | 623/22.26 |
| 5,041,140 A | 8/1991 | Teinturier | |
| 5,507,824 A * | 4/1996 | Lennox | 623/22.25 |
| 5,549,691 A | 8/1996 | Harwin | |
| 5,645,606 A | 7/1997 | Oehy et al. | |
| 5,931,870 A * | 8/1999 | Cuckler et al. | 623/22.21 |
| 2005/0246026 A1 * | 11/2005 | Lewis et al. | 623/20.15 |

FOREIGN PATENT DOCUMENTS

| | | |
|---|---|---|
| DE | 3129174 A | 2/1983 |
| DE | 88 07 947 U | 8/1988 |
| DE | 296 14 342 U | 10/1996 |
| DE | 101 59 677 A1 | 6/2003 |
| EP | 1053723 | 11/2000 |
| EP | 1532946 | 5/2005 |
| EP | 1702589 | 9/2006 |
| FR | 2793137 | 11/2000 |
| FR | 2819172 | 7/2002 |
| GB | 1409051 | 10/1975 |
| GB | 2424187 | 9/2006 |

* cited by examiner

*Primary Examiner*—Thomas J Sweet
*Assistant Examiner*—Yashita Sharma
(74) *Attorney, Agent, or Firm*—Harness, Dickey (57) ABSTRACT

A prosthesis to be implanted within a bone comprises a shell and a liner that fits within the shell. The shell comprises a bone engaging region which terminates at a first plane, and a non-bone engaging region which extends out of the first plane and at least partially defines an open mouth of the shell.

16 Claims, 7 Drawing sheets